(12) United States Patent
Burke et al.

(10) Patent No.: US 8,556,840 B2
(45) Date of Patent: Oct. 15, 2013

(54) HYPEREXTENSION BRACE

(75) Inventors: Steven Burke, Huntington Beach, CA (US); Geoffrey Garth, Long Beach, CA (US); Erik Zimmer, Oceanside, CA (US)

(73) Assignee: Aspen Medical Partners, LLC, Irvine, CA (US)

( * ) Notice: Subject to any disclaimer, the term of this patent is extended or adjusted under 35 U.S.C. 154(b) by 149 days.

(21) Appl. No.: 12/977,039

(22) Filed: Dec. 22, 2010

(65) Prior Publication Data

US 2011/0152737 A1 Jun. 23, 2011

Related U.S. Application Data

(60) Provisional application No. 61/289,247, filed on Dec. 22, 2009.

(51) Int. Cl.
*A61F 5/00* (2006.01)

(52) U.S. Cl.
USPC .......................................................... 602/19

(58) Field of Classification Search
USPC .......... 602/5, 19, 20; 128/846, 869, 870, 871, 128/875, 876; 224/259, 262, 600–605, 623, 224/627–641, 648, 649
See application file for complete search history.

(56) References Cited

U.S. PATENT DOCUMENTS

| | | | |
|---|---|---|---|
| 4,409,969 A * | 10/1983 | Will | 602/19 |
| 4,976,257 A | 12/1990 | Akin et al. | |
| 5,105,828 A | 4/1992 | Grant | |
| 5,135,471 A | 8/1992 | Houswerth | |
| 5,203,765 A | 4/1993 | Friddle, Jr. | |
| 5,295,947 A | 3/1994 | Muncy | |
| 5,318,575 A | 6/1994 | Chesterfield et al. | |
| 5,342,289 A | 8/1994 | Munny | |
| 5,437,617 A * | 8/1995 | Heinz et al. | 602/19 |
| 5,449,338 A | 9/1995 | Trudell | |
| 5,503,314 A | 4/1996 | Fiscus | |
| 5,520,619 A | 5/1996 | Martin | |
| 5,548,843 A | 8/1996 | Chase et al. | |
| 5,569,171 A | 10/1996 | Muncy | |
| 5,632,724 A | 5/1997 | Lerman et al. | |
| 5,674,187 A | 10/1997 | Zepf | |
| 5,690,260 A | 11/1997 | Aikins et al. | |
| 5,704,904 A | 1/1998 | Dunfee | |
| 5,724,993 A | 3/1998 | Dunfee | |
| 5,728,054 A | 3/1998 | Martin | |
| 5,752,640 A | 5/1998 | Proulx | |
| 5,826,766 A | 10/1998 | Aftanas | |
| 5,836,493 A | 11/1998 | Grunsted et al. | |

(Continued)

FOREIGN PATENT DOCUMENTS

| | | |
|---|---|---|
| EP | 1985264 | 10/2008 |
| WO | 2009/017499 | 2/2009 |
| WO | 2009/017949 | 2/2009 |
| WO | 2009/052031 | 4/2009 |

*Primary Examiner* — Patricia Bianco
*Assistant Examiner* — Raymond E Harris
(74) *Attorney, Agent, or Firm* — Fish & Associates, PC

(57) ABSTRACT

A posture correction brace for a person has a tightening mechanism that allows a user to pull a cord to pull down on the back of a pair of shoulder straps, thereby pulling the shoulders back to correct the person's posture. The front ends of the shoulder straps are typically also attached to the back of the wearer, to help the posture correction brace pull the shoulders back as the shoulder straps tighten.

12 Claims, 7 Drawing Sheets

(56) References Cited

U.S. PATENT DOCUMENTS

| | | |
|---|---|---|
| 5,853,379 A | 12/1998 | Ostojic |
| 5,868,292 A | 2/1999 | Stephens et al. |
| 5,950,628 A | 9/1999 | Dunfee |
| 5,954,250 A | 9/1999 | Hall et al. |
| 5,993,403 A | 11/1999 | Martin |
| 6,036,664 A | 3/2000 | Martin, Sr. et al. |
| 6,066,108 A | 5/2000 | Lundberg |
| 6,213,968 B1 | 4/2001 | Heinz et al. |
| 6,245,033 B1 | 6/2001 | Martin |
| 6,471,665 B1 | 10/2002 | Milbourn et al. |
| 6,478,759 B1 | 11/2002 | Modglin et al. |
| 6,676,617 B1 | 1/2004 | Miller |
| 6,726,643 B1 | 4/2004 | Martin |
| 6,766,532 B1 * | 7/2004 | Cabana .............................. 2/44 |
| D501,078 S | 1/2005 | Cabana |
| 7,001,350 B2 | 2/2006 | Grosso |
| 7,025,737 B2 | 4/2006 | Modglin |
| 7,083,585 B2 | 8/2006 | Latham |
| 7,316,660 B1 | 1/2008 | Modglin |
| 7,322,950 B2 | 1/2008 | Modglin |
| 2001/0020144 A1 * | 9/2001 | Heinz et al. ..................... 602/19 |
| 2002/0042584 A1 * | 4/2002 | Rue ................... 602/5 |
| 2005/0137508 A1 | 6/2005 | Miller |
| 2005/0154337 A1 | 7/2005 | Meyer |
| 2006/0011690 A1 | 1/2006 | Bareno |
| 2006/0155229 A1 | 7/2006 | Ceriani et al. |
| 2008/0045873 A1 * | 2/2008 | Zours .............................. 602/19 |
| 2008/0302839 A1 | 12/2008 | Murdoch et al. |
| 2009/0127308 A1 | 5/2009 | Mori et al. |
| 2009/0275871 A1 | 11/2009 | Liu |

\* cited by examiner

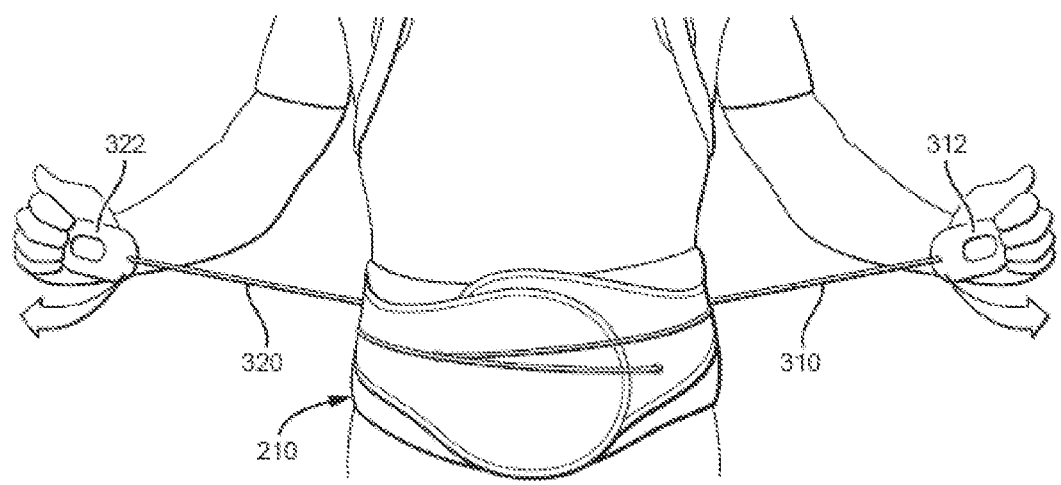
FIG. 7C
FIG. 7D
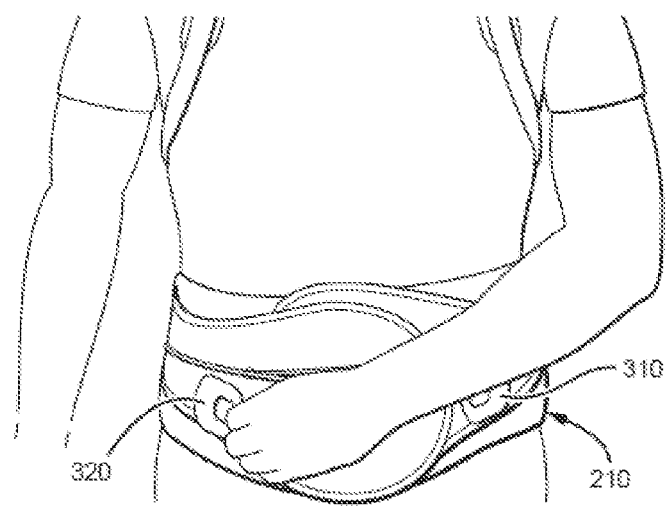

HYPEREXTENSION BRACE

This application claims priority to provisional application Ser. No. 61/289,247, filed Dec. 22, 2009, which is incorporated herein by reference in its entirety.

FIELD OF THE INVENTION

The field of the invention is orthotics for posture correction.

BACKGROUND

Existing braces are limited in that there is no one-size fits all. Users with different height and torso widths need different sizes. There needs to be a brace that can be used for different users and yet still provide a tight, comfort, and proper fit to the user's body.

U.S. Pat. No. 5,548,843 to Chase et al. teaches a support belt in which the user can pull the belt straps to secure the shoulders. However, only the front portion of Chase's shoulder straps can be shortened, which tends to pull the shoulders forward instead of back. This hurts the wearer's posture, and could be extremely detrimental where the user has a medical issue with his posture, for instance where the wearer has a thoracic kyphosis.

WO 2009/052031 to Sandifer et al (the '031 brace) teaches a brace where a user can pull "fastening pads" around the waist to tighten the abdominal and at the same time tighten the user's shoulder straps. However, the '031 brace is not adjustable for different users, and specifically teaches that in order for the brace to fit a different user than the user for which it is designed, a physician would have to cut the straps. The '031 brace also teaches a pair of shoulder straps attached to a spinal frame member via rivets around the midsection of the post, which is rigid along the spinal frame member.

WO 2009/017499 to Sandifer et al (the '499 brace) teaches a brace with a spinal frame member that can be adjusted along with the shoulder strap. However, the '499 brace requires the spinal frame to be adjusted via screws in pre-drilled holes and is not movable once the screws are in place. If the spinal frame needs to be adjusted, the brace must first be removed from the user and then the screws need to be adjusted. If the spinal frame needs to be adjusted to a position in between the pre-drilled holes, a new hole would need to be drilled or a new spinal frame created.

U.S. Pat. No. 5,954,250 to Hall also teaches a harness with an adjustable spinal frame, however, like Sandifer, Hall's spinal frame must be adjusted by another person, or when the wearer is not wearing Hall's harness.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Thus, there is still a need in the art for improved adjustable braces that help correct a wearer's posture.

SUMMARY OF THE INVENTION

The inventive subject matter provides apparatus, systems and methods in which a posture correction brace pulls the shoulders back of a person with a pull cord that inferiorly adjusts a posterior portion of each of the straps along a person's back when the cord is pulled. As used herein, the term "cord" means any device flexible at room temperature that mechanically pulls a device attached to one end of the cord with a dvice attached to another end of the cord, for example a rope, belt, monofilament, braid, or string. As used herein, the term "inferiorly adjusts" means to adjust a device downwards from the person's head towards the person's feet. As used herein, the term "posterior" means any part of the body behind the midline of the person, and preferably along the rear surface of the person (which excludes the side surfaces which start along the surface of the person's arms or ears. As used herein, the term "along the person's back" means that the strap is pulled within a 45 degree angle along the wearer's midline, and more preferably within a 30 degree or a 15 degree angle along the wearer's midline.

Generally, the two posterior portions of the shoulder straps couple to a latch on the back of the wear that is pulled down as the pull cord is pulled, although the pull cord itself could attach to each posterior portion of the shoulder straps separately without departing from the scope of the invention. Preferably, the ends of the shoulder straps are attached to a hinge, or the shoulder straps comprise a single strap that threads through a loop to form two separate shoulder straps. As used herein, a "loop" is any structure that a cord could be threaded through to change a pulling direction of the cord, such as a hole, hook, pulley, or corner. Shoulder straps could be made from any suitable material, for example leather, vinyl, rubber), and is preferably flexible. The shoulder strap could have padding coupled to a shoulder area of the strap to help prevent chafing while the strap is adjusted inferiorly.

The brace is preferably configured such that the pull cord could be pulled forward by the wearer while the brace is worn, which would then pull back on the shoulder straps, thereby pulling back on the wearer's shoulders as the pull cord is drawn. For example, one end of the cord could be coupled to the shoulder straps, and the cord could be threaded orthogonally through a loop to run forward along the waist of the user. This would allow the user to pull one end of the cord anteriorly forward, which would then translate that three to pull the other end of the cord inferiorly downward along the back.

The pull cord and the posterior portion of each of the shoulder straps could be coupled via a slider that rides along a vertical rail to ensure that the shoulder straps are adjusted approximately parallel to the wearer's midline. The slider could have a second tightening mechanism that ensures that the pull cord remains taught after the shoulder straps are pulled in place. Alternatively or in addition to the tightening mechanism, the rail could comprise matching indents or detents that match the slider to allow a user to "click" through a plurality of adjustment positions. In an exemplary embodiment, the slider comprises a base and an adjustable extender that allows a wearer to first adjust a range of movement for the posterior portions of the shoulder straps before adjusting the height of the posterior portions of the shoulder straps.

Preferably an anterior portion of the pull cord, such as the end of the pull cord, is coupled to a pull tab that is easily grasped by the wearer. In an exemplary embodiment, the pull tab is coupled to a belt around the waist of the wearer for easy access, for example using a hook and loop fastener, a button, a pocket, or a magnetic coupling on the belt. Anterior portions of the shoulder straps, such as the anterior ends of the shoulder straps, could be coupled to a posterior portion of the belt, which would further assist in drawing the wearer's shoulders back as the posterior portions of the shoulder strap are tightened.

The belt generally wraps around the wearer, preferably about the lumbar area. An exemplary belt has a stiff portion around the lumbar area of the wearer to support the lumbar area of the wearer. The belt could also have an adjustment mechanism that tightens the belt around the wearer, such as a strap threaded through a loop, a cloth tie, or overlapping hook and loop anterior ends. Preferably, the adjustment mechanism comprises one or more pulley systems that tighten the belt around the wearer, for example around the lumbar area of the wearer, the lateral area of the wearer, or evenly around the wearer. A second pull cord could be coupled to the belt's adjustment mechanism such that the second pull cord could be pulled forward by the wearer to tighten the adjustment mechanism while the brace is worn. In an exemplary embodiment, the first and second pull cords are positioned on opposite sides of the wearer, such that the wearer could pull forward on both pull cords simultaneously to both pull the shoulders back and to pull the belt taught.

The length of the shoulder straps is preferably also adjustable to accommodate wearers of different heights. Additionally, anterior portions of the shoulder straps could be pulled towards one another using a chest strap or buckle, providing for a snug fit. Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 7A-7D show perspective views of the alternative embodiment of FIG. 2 with a wearer adjusting the posterior portion of each of the shoulder straps.

DETAILED DESCRIPTION

Figure 1A:
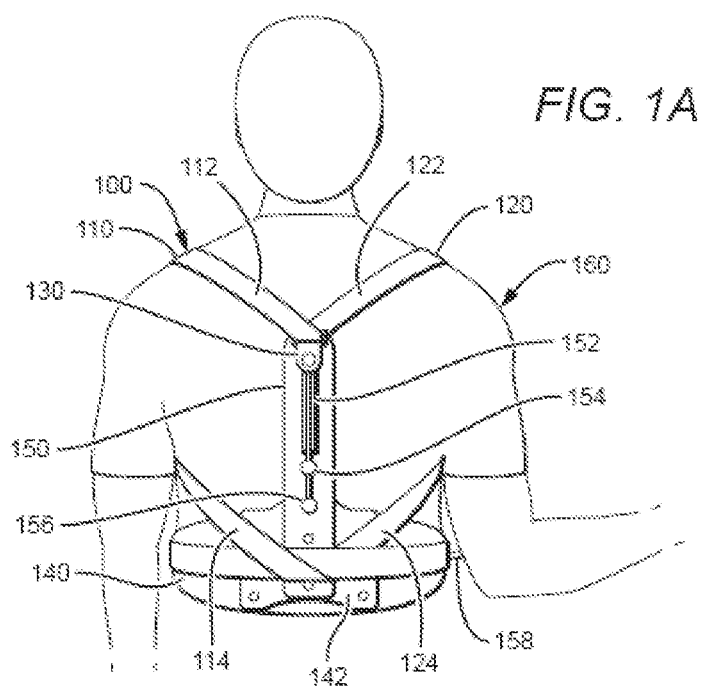
FIGS. 1A-1B are rear perspective views of an embodiment of the current inventive subject matter with the shoulder straps comprising a single strap wrapped around both shoulders of the wearer.
Figure 1B:
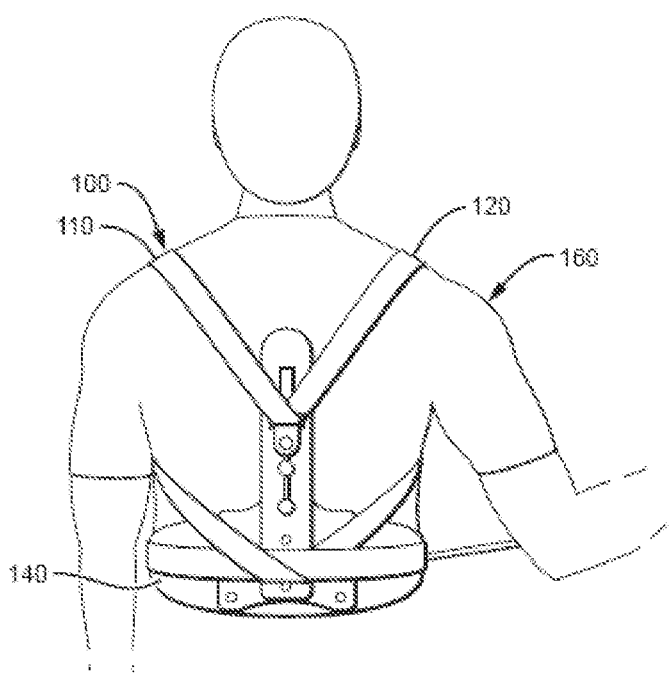

In FIGS. 1A-1B, an exemplary posture correction brace 100 has a pair of shoulder straps 110 and 120 coupled to a hinge 130 that is joined to a belt 140 via slider 150. While shoulder straps 110 and 120 are coupled to hinge 130 using a thin hole, the shoulder straps could be coupled to the hinge using any suitable loop. Shoulder straps 110 and 120 comprise a single strap that divides into two separate components through hinge 130. Shoulder straps 110 and 120 have superior sections 112 and 122, respectively and inferior sections 114 and 124, respectively. Superior sections 112 and 122 are coupled to hinge 130, which draws those sections inferiorly along wearer 160's back as hinge 130 is drawn downwards along slider 150. Inferior sections 114 and 124 are coupled to posterior portion 142, and then around the waist of wearer 160. The anterior ends(not shown) of straps 110 and 120 then meet at the front of wearer 160, such that wearer 160 could then tighten belt 140 by manipulating the anterior ends, for example by simply tying the ends together or by threading the ends through a loop.

As shown, slider 150 comprises a rail 152 along which hinge 130 slides. Hinge 130 is sized and dimensioned to slide towards or away from pulleys 154 and 156 when cord 158 is pulled or loosened, respectively. One end of cord 158 is coupled to hinge 130, and cord 158 threads through pulleys 154 and 156 such that the other end of cord 158 rests on a side of the wearer. This allows the wearer to draw hinge 130 downwards along slider 150 by pulling forward on cord 158 with a pull-tab. FIG. 1A depicts slider 150 in its superior-most position when cord 158 is loosened, while FIG. 1B depicts slider 150 in its inferior-most position when cord 158 is pulled taught.

Figure 2:
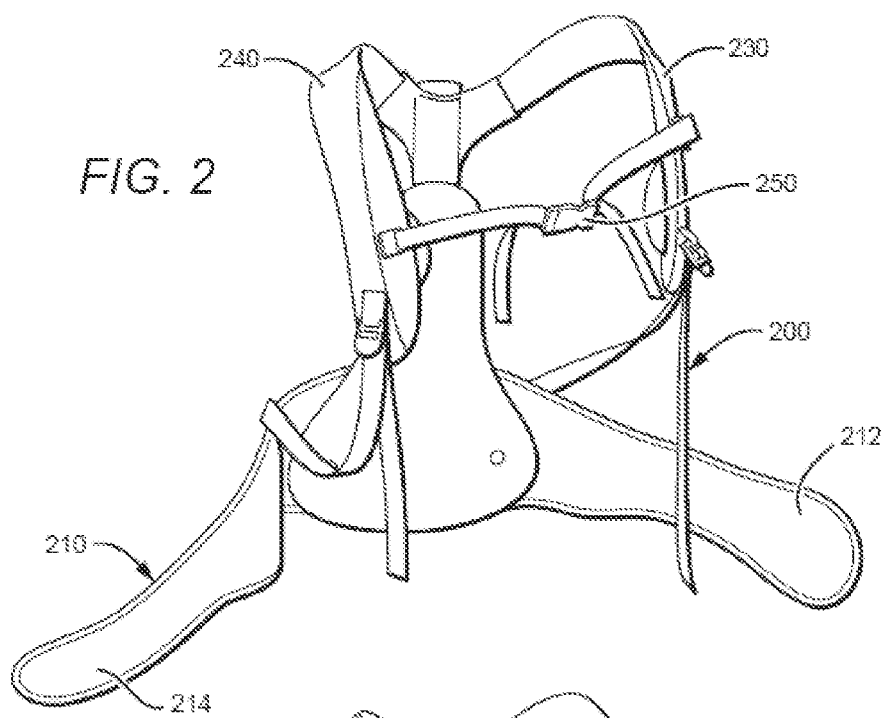
FIG. 2 shows a front perspective view of an alternative embodiment of the current inventive subject matter.
Figure 3:
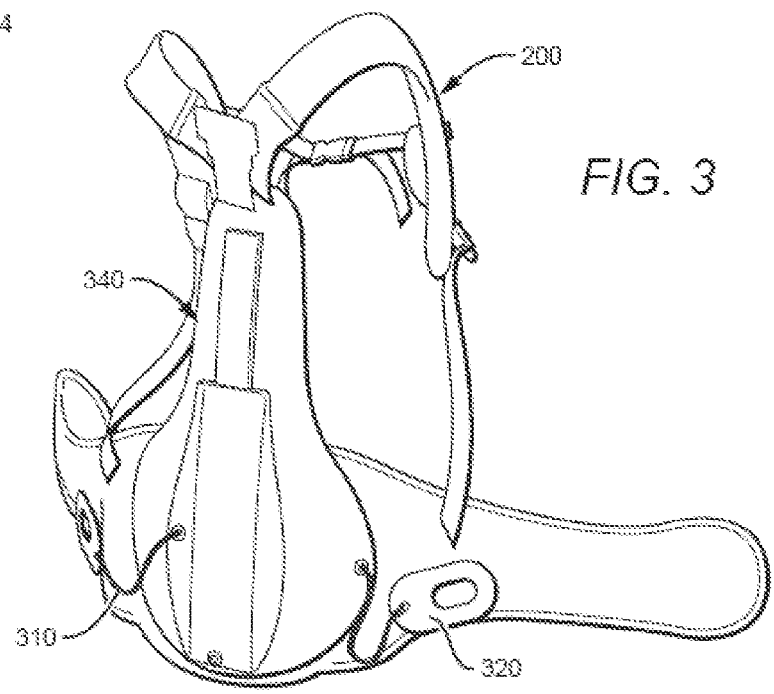
FIG. 3 shows a rear perspective views of the alternative embodiment in FIG. 2.

In FIG. 2, an alternative posture correction brace 200 has belt 210, left shoulder strap 230, right shoulder strap 240, and chest buckle 250, FIG. 3 shows a rear view of brace 200 with left cord 310, right cord 320, and slider 340.

Figure 4A:
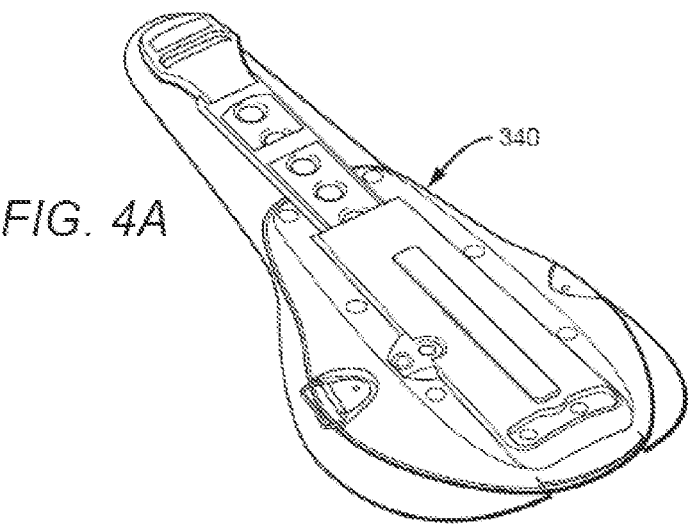
FIGS. 4A-4B show a perspective and an exploded view of the slider used in the alternative embodiment of FIG. 2.
Figure 4B:
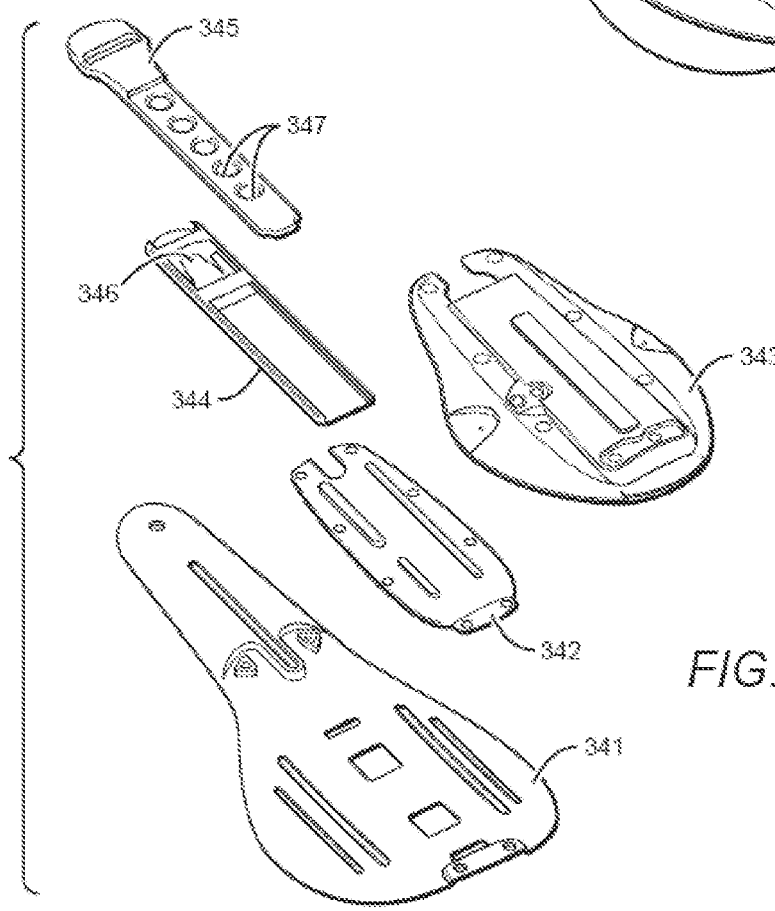

FIGS. 4A and B is an exploded view of slider 340, with base panel 341, track base 342, track cover 343, sheath 344, and extender 345. Sheath 344 couples to extension 345 by threading sheath detent 346 through extender holes 347. By threading sheath detent 346 through different extender holes 347, a user effectively adjusts a range of movement for posterior portions of left shoulder strap 230 and right shoulder strap 240, since both are attached to the superior end of extender 345. After the extender 345 length is adjusted, the extender 345 could be inserted into track base 342 which is then held against the track by sandwiching base panel 341 against track cover 343, which both effectively limit a travel of the extender 345 approximately to the length of sheath 344.

Figure 5B:
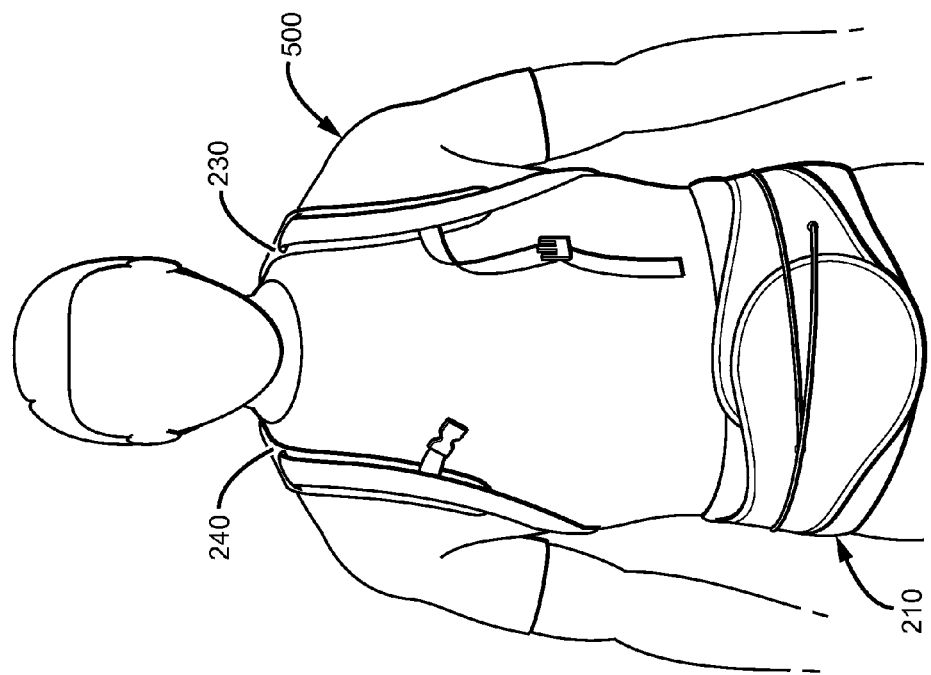
FIGS. 5A-5B show perspective views of the alternative embodiment of FIG. 2 with a wearer adjusting a circumferential pressure.
Figure 5A:
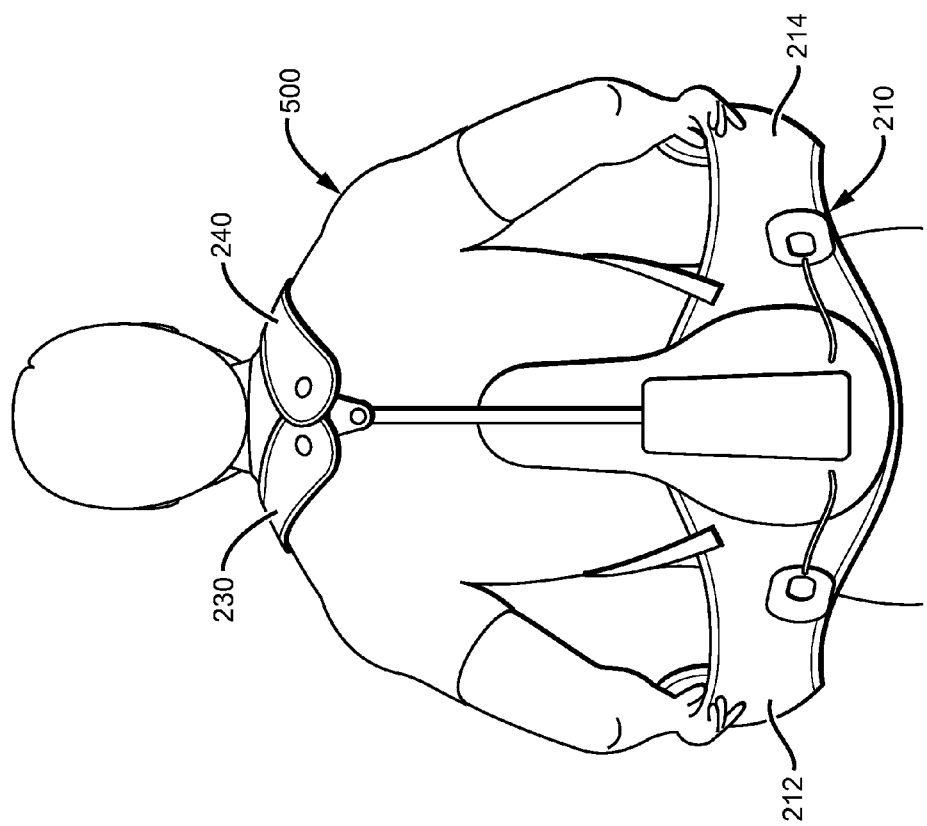

FIGS. 5A-5B show perspective views of a wearer 500 putting on brace 200 and adjusting belt 210. First, wearer 500 threads his left and right arms through the left shoulder strap 230 and right shoulder strap 240, respectively. Belt 210 has left anterior portion 212 and right anterior portion 214 that overlap one another around the stomach of wearer 500 to provide a snug fit, such as in copending application Ser. No. 12/394,867, which is incorporated herein by reference.

Figure 6A:
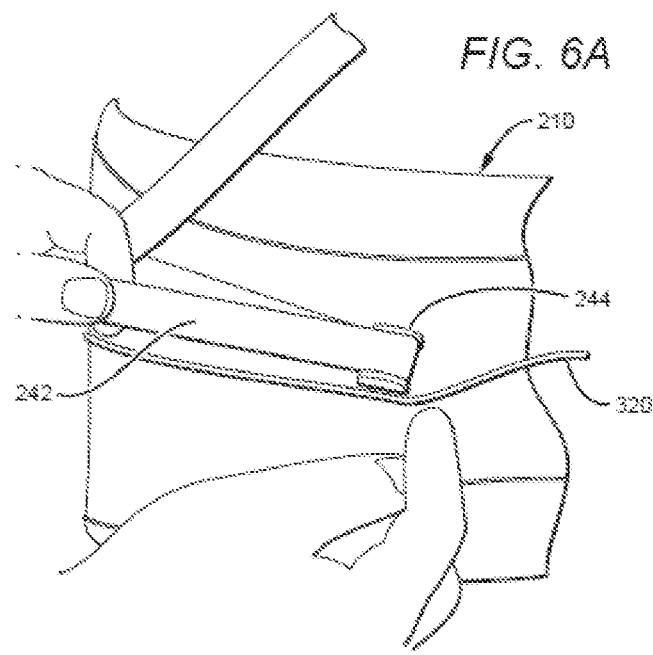
FIGS. 6A-6B show perspective views of the alternative embodiment of FIG. 2 with a wearer adjusting the length of the shoulder straps
Figure 6B:
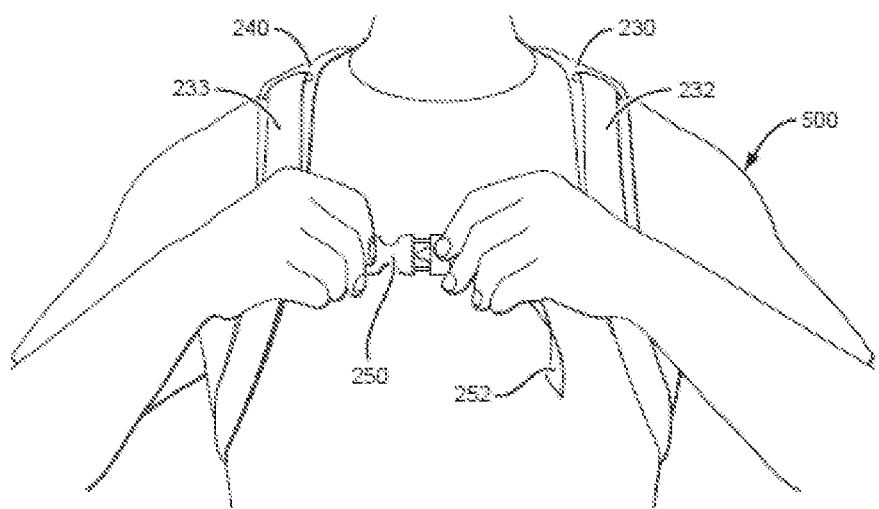
Figure 7A:
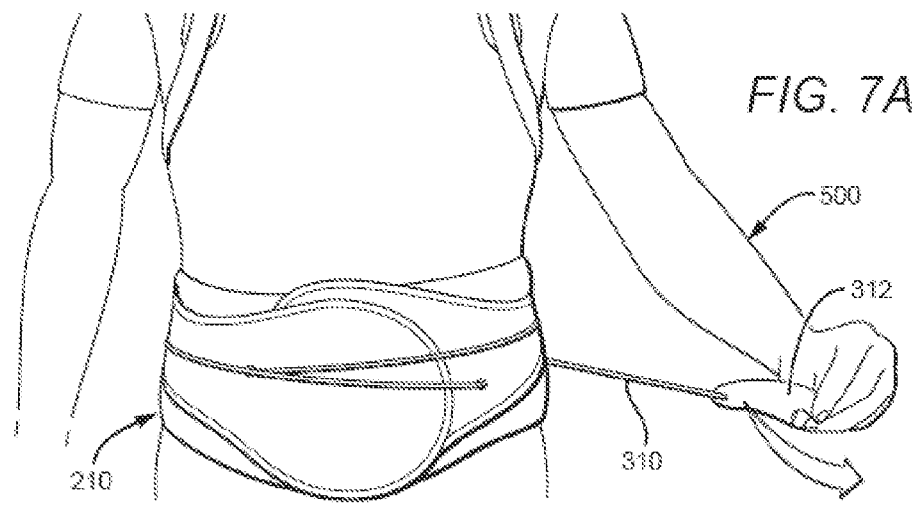
Figure 7B:
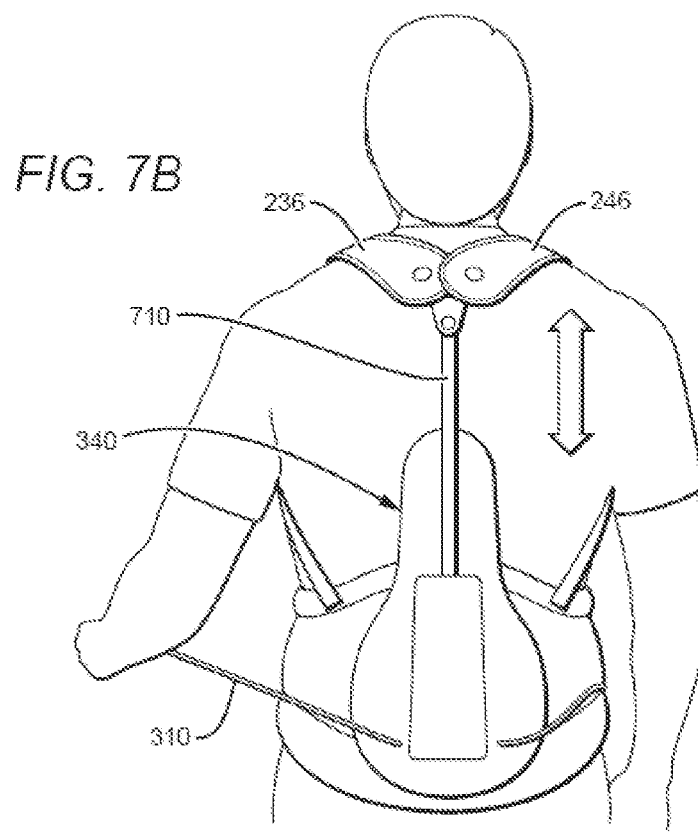

FIGS. 6A-6B show perspective views of wearer 500 then adjusting left shoulder strap 230 and right shoulder strap 240 about wearer 500. Posterior portion 242 of right shoulder strap 240 couples to the posterior portion of belt 210 via loop clasp 244, which could be opened to allow a user to lengthen or shorten the effective length of right shoulder strap 240. Wearer 500 could then tighten the shoulder straps using chest buckle 250. Chest buckle 250 has a strap 252 that could be used to draw anterior portion 232 of left shoulder strap 230 towards anterior portion 233 of right shoulder strap 240, creating a snug fit.

FIGS. 7A-7D show perspective views of wearer 500 inferiorly adjusting posterior portion 246 of right shoulder strap and posterior portion 236 of left shoulder strap 230 inferiorly along wearer 500's back. Since posterior portion 236 of left shoulder strap 230 and posterior portion 246 of right shoulder strap 240 are coupled to slider 340 using strap 710, as wearer 500 pulls left cord 310, extender 345 is pulled down along track base 342 within slider 340. This effectively pulls the shoulders of wearer 500 back, correcting the posture of wearer 500 and holding the shoulders back.

Right cord 320 is coupled to a lumbar adjustment mechanism similar to that disclosed in copending application Ser. No. 12/394,867, which allows a user to adjust both belt 210 and slider 340 by pulling on right cord 320 and left cord 310, respectively, as shown in FIG. 7C. Pull tabs 312 and 322 are then coupled to the front of belt 210 using hook and loop fasteners. While pull tabs 312 and 322 are coupled to the belt using standard hook and loop fasteners, pull tabs 312 and 322 could be coupled to the belt in any other suitable manner without departing from the scope of the invention.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A posture correction brace for a person, comprising:
   a pair of shoulder straps comprising a left strap and a right strap, each of which has anterior and posterior portions; and
   a single pull cord coupled to the pair of shoulder straps that inferiorly adjust the posterior portion of each of the left and right straps simultaneously along the person's back when the cord is pulled and while the brace is worn; and wherein the pull cord adjusts the posterior portion of each of the left and right straps through a slider that rides along a rail.

2. The brace of claim 1, further comprising a belt that extends around the person.

3. The brace of claim 2, wherein the pull cord extends from the belt.

4. The brace of claim 2, further comprising a second pull cord that tightens the belt around the person.

5. The brace of claim 4, further comprising a pulley system that tightens the belt around a lumbar region of the person.

6. The brace of claim 1, wherein the slider comprises a base and an adjustable extender.

7. The brace of claim 1, further comprising a chest strap that pulls an anterior portion of each of the left and right-straps towards one another.

8. The brace of claim 2, further comprising a pull-tab coupled with the pull cord, wherein the pull-tab is attachable to the belt using a hook and loop fastener.

9. The brace of claim 2, wherein an anterior portion of each of the left and right straps couples to a posterior portion of the belt.

10. The brace of claim 1, wherein a length of at least one of the left and right-straps is adjustable.

11. The brace of claim 1, wherein the pull cord is threaded orthogonally to allow the person to adjust the posterior portion of each of the left and right-straps inferiorly by pulling the pull cord anteriorly.

12. A posture correction brace for a wearer, comprising:
    left and right shoulder straps, each of which has an anterior and posterior portion, wherein the left and right shoulder straps are coupled to a slider;
    wherein the slider is configured to move in a superior or inferior direction along a rail, and is coupled to a belt configured to wrap around a waist of a wearer; and
    a cord coupled to the slider such that pulling the cord adjusts a vertical position of the slider and simultaneously adjusts a posterior portion of each of the left and right shoulder straps.

* * * * *